United States Patent
Woo et al.

(10) Patent No.: US 12,249,415 B2
(45) Date of Patent: Mar. 11, 2025

(54) RADIOPHARMACEUTICAL DISTRIBUTION IMAGE GENERATION SYSTEM AND METHOD USING DEEP LEARNING

(71) Applicant: KOREA INSTITUTE OF RADIOLOGICAL & MEDICAL SCIENCES, Seoul (KR)

(72) Inventors: Sang Keun Woo, Seoul (KR); Sang Moo Lim, Seoul (KR); Kyo Chul Lee, Seoul (KR); Wook Kim, Seongnam-si (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 356 days.

(21) Appl. No.: 17/787,845

(22) PCT Filed: Jul. 2, 2020

(86) PCT No.: PCT/KR2020/008658
§ 371 (c)(1),
(2) Date: Jun. 21, 2022

(87) PCT Pub. No.: WO2021/137371
PCT Pub. Date: Jul. 8, 2021

(65) Prior Publication Data
US 2023/0029695 A1    Feb. 2, 2023

(30) Foreign Application Priority Data
Jan. 2, 2020 (KR) .................. 10-2020-0000523

(51) Int. Cl.
*G16H 30/20* (2018.01)
*G06T 7/00* (2017.01)
(Continued)

(52) U.S. Cl.
CPC .......... *G16H 30/20* (2018.01); *G06T 7/0012* (2013.01); *G06T 7/269* (2017.01); *G16H 20/10* (2018.01);
(Continued)

(58) Field of Classification Search
CPC ........ G16H 30/20; G16H 20/10; G16H 30/40; G16H 50/50; G06T 7/0012; G06T 7/269;
(Continued)

(56) References Cited

U.S. PATENT DOCUMENTS 10,915,990 B2 * 2/2021 Lebel ..................... G06V 10/82
11,972,567 B2 * 4/2024 Lee ........................ G06T 7/0014
(Continued)

FOREIGN PATENT DOCUMENTS

CN  101542530 A   9/2009
JP  6530128 B1    6/2019
(Continued)

OTHER PUBLICATIONS

Amended claims filed after receipt of (European) search report for EP4086918 dated Jul. 31, 2024 (Year: 2024).*
(Continued)

*Primary Examiner* — Juan A Torres

(57) ABSTRACT

The present invention relates to a radiopharmaceutical distribution image generation system and method using deep learning and, more specifically, to a radiopharmaceutical distribution image generation system and method using deep learning, wherein dynamic medical images collected from multiple patients and a time-radiation dose distribution curve for each organ can be learnt through a deep learning network and a spatial distribution image of a radiopharmaceutical can be generated from a static medical image acquired from a specific patient. According to the present invention, even when a medical image is acquired only for
(Continued)

a specific time after a radiopharmaceutical is injected into a patient, a spatial distribution image of the radiopharmaceutical can be acquired across the entire time by using the deep learning network, and quantitative analysis of the radiopharmaceutical can be performed by calculating a time-radiation dose distribution curve on the basis thereof.

6 Claims, 4 Drawing Sheets

(51) Int. Cl.
    *G06T 7/269*     (2017.01)
    *G16H 20/10*     (2018.01)
    *G16H 30/40*     (2018.01)

(52) U.S. Cl.
    CPC ... *G16H 30/40* (2018.01); *G06T 2207/20081* (2013.01)

(58) Field of Classification Search
    CPC ......... G06T 2207/20081; G06T 7/0016; G06T 2207/10016; G06T 2207/10081; G06T 2207/10104; G06T 2207/20084
    USPC .......................................................... 382/128
    See application file for complete search history.

(56) References Cited

U.S. PATENT DOCUMENTS

| | | | |
|---|---|---|---|
| 2019/0130565 A1* | 5/2019 | Lee | G06N 3/08 |
| 2019/0192880 A1* | 6/2019 | Hibbard | G16H 30/20 |
| 2019/0197358 A1* | 6/2019 | Madani | G06N 3/045 |

FOREIGN PATENT DOCUMENTS

| | | |
|---|---|---|
| KR | 10-2019-0046471 A | 5/2019 |
| KR | 10-2019-0088371 | 7/2019 |
| KR | 10-2019-0103926 A | 9/2019 |
| KR | 10-2019-0127247 A | 11/2019 |

OTHER PUBLICATIONS

K. Gong et al., "Direct patlak reconstruction from dynamic PET using unsupervised deep learning", Proc. SPIE 11072, 15th International Meeting on Fully Three-Dimensional Image Reconstruction in Radiology and Nuclear Medicine, 110720R, May 28, 2019.

Z. Xie et al., "Generative adversarial networks based regularized image reconstruction for PET", Proc. SPIE 11072, 15th International Meeting on Fully Three-Dimensional Image Reconstruction in Radiology and Nuclear Medicine, 110720P, May 28, 2019.

The Extended European Search Report for European Patent Application No. 20910482.7, dated Jan. 11, 2024.

Fumio Hashimoto et al., "Dynamic PET Image Denoising Using Deep Convolutional Neural Networks Without Prior Training Datasets," IEEE Access, 2019, pp. 96594-96603, vol. 7.

Kuang Gong et al., "Machine Learning in PET: From Photon Detection to Quantitative Image Reconstruction," Proceedings of the IEEE, Jan. 1, 2020, pp. 51-68, vol. 108.

Karl D. Spuhler et al., "Synthesis of Patient-Specific Transmission Data for PET Attenuation Correction for PET/MRI Neuroimaging Using a Convolutional Neural Network," The Journal of Nuclear Medicine, Apr. 1, 2019, pp. 555-560, vol. 60.

* cited by examiner

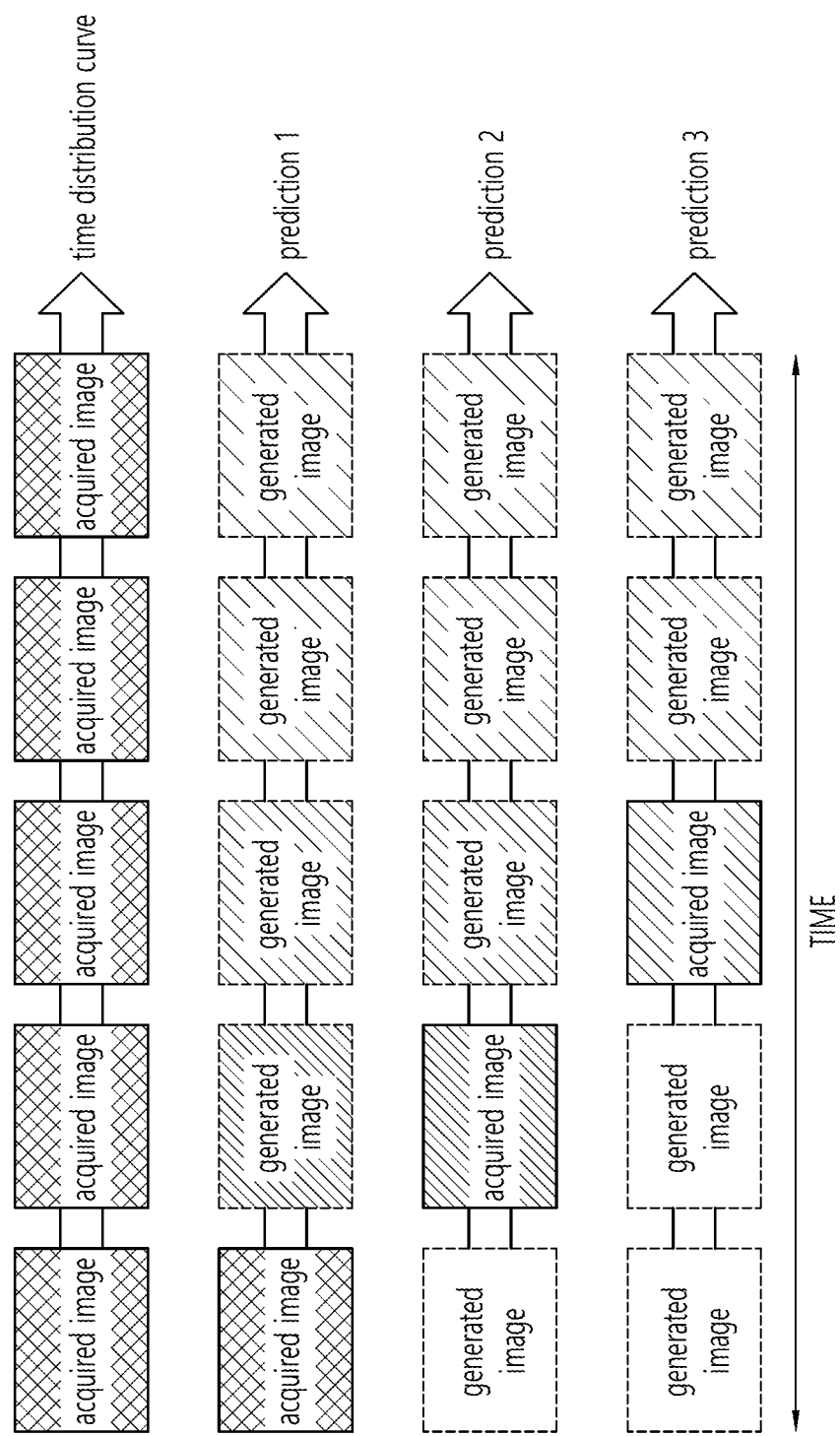

RADIOPHARMACEUTICAL DISTRIBUTION IMAGE GENERATION SYSTEM AND METHOD USING DEEP LEARNING

TECHNICAL FIELD

The disclosure relates to a system and method for generating a radiopharmaceutical distribution image based on deep learning, and more particularly to a system and method for generating a radiopharmaceutical distribution image based on deep learning, in which dynamic medical images collected from multiple patients and time-radiation dose distribution curves according to organs are learned through a deep learning network, and a spatial distribution image of radiopharmaceuticals is generated based on a static medical image acquired from a specific patient.

BACKGROUND ART

Positron emission tomography (PET) and single-photon emission computed tomography (SPECT) images are medical imaging devices that detect energy emitted as labelled radionuclides decay, which are useful as medical imaging tools to diagnose a patient and evaluate treatment response. In particular, the PET and the SPECT have advantages in that quantitative analysis is possible based on the intensity of an image.

Research on the quantitative analysis of images based on the PET and the SPECT is divided into a static medical image analysis that injects radiopharmaceuticals for diagnosis or treatment and analyzes intake in some specific time, and a dynamic medical image analysis that quantitatively analyzes the change in an absorption rate of radiopharmaceuticals over time after injection of radiopharmaceuticals.

The dynamic medical image analysis includes the processes of administering radiopharmaceuticals into a patient's body before acquiring medical images, and then continuously acquiring images while waiting until the radiopharmaceuticals are sufficiently absorbed in a target area, and performing a quantitative analysis based on a single acquired medical image. Representatively, an analysis using $^{18}$F-FDG belongs to the dynamic medical image analysis. $^{18}$F-FDG PET imaging is performed by intravenously injecting $^{18}$F-FDG into a patient's body and acquiring images for about 20 minutes after one hour.

The quantitative analysis based on the dynamic medical images provides information about change in an absorption rate of the radiopharmaceuticals over time, which is not provided by the static medical images, because the images are continuously acquired for a predetermined period of time as the acquisition of the image is started concurrently with injection of radiopharmaceuticals. However, unlike the acquisition of the static medica images, the acquisition of the dynamic medical images is very inconvenient for a patient because s/he has to lie on imaging equipment for a long time.

Consequently, the analysis based on the static medical images is less inconvenient for a patient because the medical images are acquired for a short time. However, the analysis based on the static medical images has a disadvantage in that the information about change in the absorption rate of the radiopharmaceuticals over time is not reflected.

On the other hand, the analysis based on the dynamic medical images can accurately evaluate the information about the change in the absorption rate of the radiopharmaceuticals in the target area over time, but has a problem that it is burdensome for a patient because acquisition of all the medical images over time is needed.

DISCLOSURE

Technical Problem

An aspect of the disclosure is to provide a system and method for generating a radiopharmaceutical distribution image based on deep learning, in which dynamic medical images collected from multiple patients and time-radiation dose distribution curves according to organs are learned through a deep learning network, and a spatial distribution image of radiopharmaceuticals is generated based on a static medical image acquired from a specific patient.

Technical Solution

According to an embodiment of the disclosure, there may be provided a radiopharmaceutical distribution image generation system using deep learning, the system including: a dynamic medical image acquisition unit configured to acquire dynamic medical images by continuously collecting medical images of a patient concurrently with injection of radiopharmaceuticals; a distribution curve acquisition unit configured to acquire a time-radiation dose distribution curve, which represents a radiation dose for each organ of a human body over time, from the dynamic medical images; a static medical image acquisition unit configured to acquire static medical images for a specific period of time after the injection of the radiopharmaceuticals; a deep-learning image generation network configured to predict and generate medical images corresponding to times before and after the static medical images by collecting and learning the dynamic medical images of multiple patients and the corresponding time-radiation dose distribution curve; and a spatial distribution image acquisition unit configured to acquire a spatial distribution image of the radiopharmaceuticals from the static medical images and the generated medical images.

Preferably, the deep learning network may include: a deep learning unit configured to collect and learn the dynamic medical images of the multiple patients and the corresponding time-radiation dose distribution curve; and an image generation unit configured to predict and generate the medical images corresponding to times before and after the static medical images are taken.

Preferably, the deep learning network may use a generative adversarial network (GAN) to generate the medical images according to the dynamic medical images and the corresponding time-radiation dose distribution curve.

Preferably, the system may further include a distribution curve predictor configured to acquire the time-radiation dose distribution curve by acquiring a radiation dose and a position of each region over time from the spatial distribution image.

According to an embodiment of the disclosure, there may be provided a method performed by a radiopharmaceutical distribution image generation system using deep learning, the method including: (a) acquiring dynamic medical images by continuously collecting medical images of a patient concurrently with injection of radiopharmaceuticals; (b) acquiring a time-radiation dose distribution curve, which represents a radiation dose for each organ of a human body over time, from the dynamic medical images; (c) collecting the dynamic medical images of multiple patients and the corresponding time-radiation dose distribution curve and learning through a deep learning network; (d) acquiring static medical images for a specific period of time after the injection of the radiopharmaceuticals; (e) predicting and generating medical images corresponding to times before and after the static medical images through the deep learning network; and (f) acquiring a spatial distribution image of the radiopharmaceuticals from the static medical images and the generated medical images.

Advantageous Effects

According to the disclosure, even when medical images are acquired only for a specific period of time after injecting radiopharmaceuticals into a patient, a spatial distribution image of the radiopharmaceuticals is acquired for the entire time through a deep learning network, and thus a time-radiation dose distribution curve is calculated to thereby perform the quantitative analysis of the radiopharmaceuticals.

DESCRIPTION OF DRAWINGS

FIG. 4 is a view illustrating that an image is generated for each time from static medical images and a time-radiation dose distribution curve is extracted.

BEST MODE

The disclosure can be variously modified and include various embodiments, and thus specific embodiments will be illustrated in the accompanying drawings, and described in detail below. However, it will be understood that the disclosure is not limited to the specific embodiments but encompass all changes, equivalents and alternatives within the technical sprit and scope of the disclosure.

The terms 'first,' 'second,' etc. may be used in describing various elements, but the elements are not limited by these terms. The terms are used only for the purpose of distinguishing one element from another. For example, a first element referred to as a first element in one embodiment can be referred to as a second element in another embodiment without departing from the scope of the disclosure.

The terminologies used in the disclosure are intended to merely describe a specific embodiment, but not limit the disclosure. Unless the content clearly indicates otherwise, singular forms are intended to include plural forms as well. It will be further understood that the terms "include," "have," etc. used in the disclosure are intended to specify the presence of stated features, integers, steps, operations, elements, components, or combinations thereof, but not preclude the presence or addition of one or more other features, integers, steps, operations, elements, components, or combinations thereof.

Unless defined otherwise, all terms used herein including technical or scientific terms have the same meanings as those generally understood by a person having ordinary knowledge in the art to which the disclosure pertains.

The terms such as those defined in generally used dictionaries are construed to have meanings matching those in the context of related technology and, unless clearly defined otherwise, are not construed to be ideally or excessively formal.

Blow, embodiments of the disclosure will be described in more detail with reference to the accompanying drawings. Like numerals refer to like elements throughout.

Figure 1:
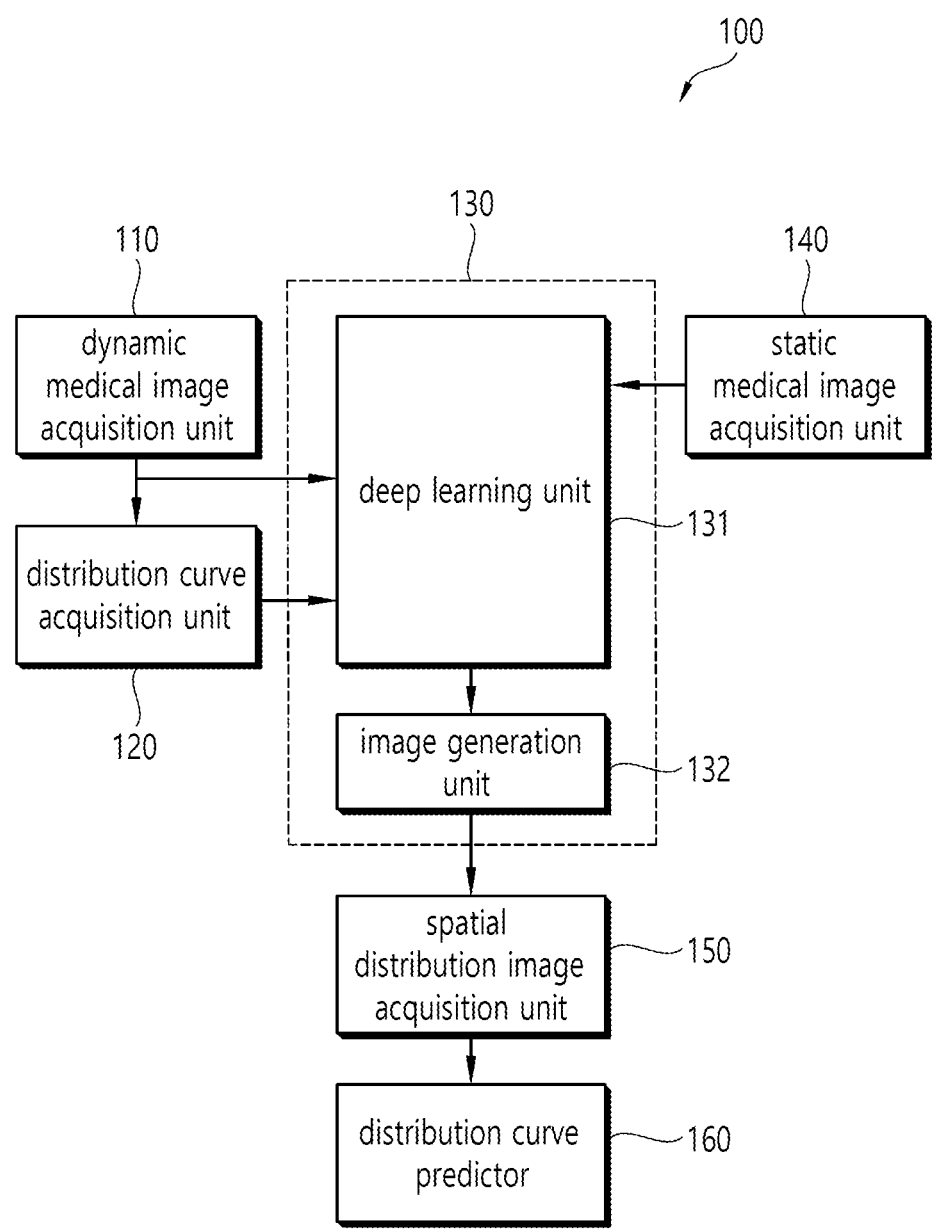
FIG. 1 is a block diagram of a radiopharmaceutical distribution image generation system using deep learning according to the disclosure.
Figure 2:
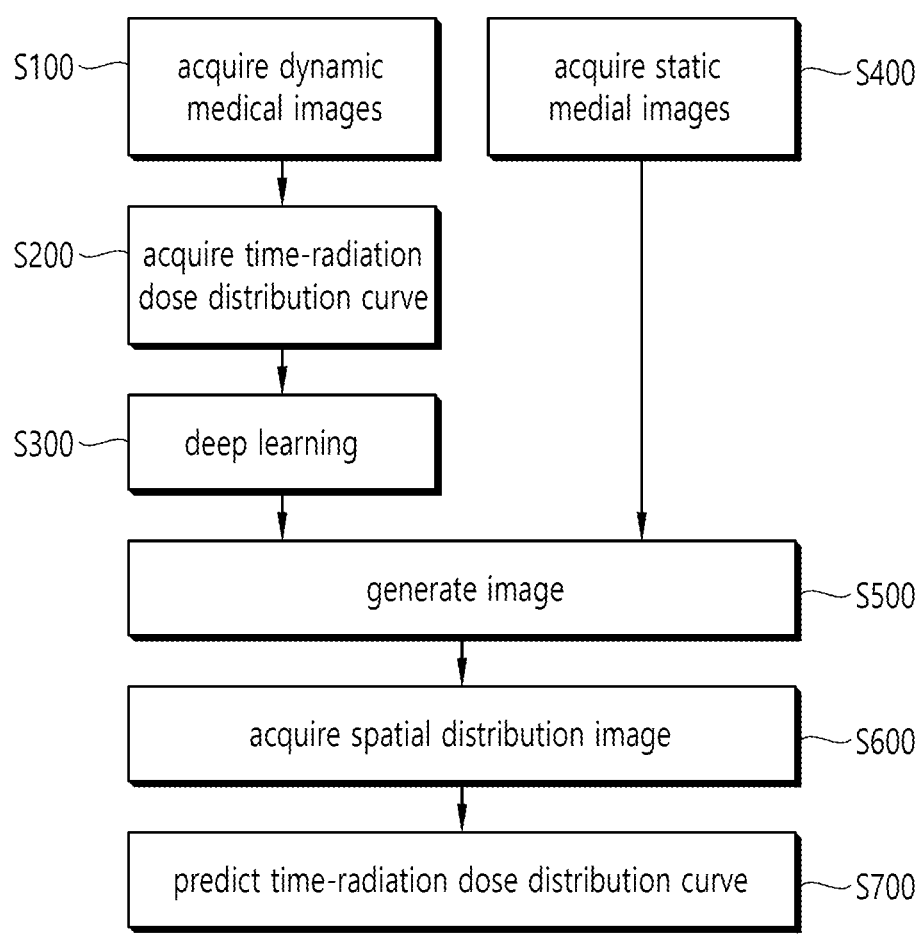
FIG. 2 is a flowchart of a radiopharmaceutical distribution image generation method using deep learning according to the disclosure.

FIG. 1 is a block diagram of a radiopharmaceutical distribution image generation system using deep learning according to the disclosure, and FIG. 2 is a flowchart of a radiopharmaceutical distribution image generation method using deep learning according to the disclosure.

The radiopharmaceutical distribution image generation method using the deep learning according to the disclosure refers to and is essentially the same as a method performed by the radiopharmaceutical distribution image generation system using the deep learning according to the disclosure, and therefore they will be described below together.

Referring to FIG. 1, a radiopharmaceutical distribution image generation system 100 using the deep learning according to the disclosure may include a dynamic medical image acquisition unit 110, a distribution curve acquisition unit 120, a deep learning network 130, a static medical image acquisition unit 140, and a spatial distribution image acquisition unit 150, and may additionally include a distribution curve predictor 160.

First, the dynamic medical image acquisition unit 110 acquires dynamic medical images by continuously collecting a patient's medical images concurrently with injection of radiopharmaceuticals (S100). To spatially analyze diagnostic medical images, a positron emission tomography-computed tomography (PET-CT) scanner may be used. The diagnostic medical images acquired by the PET-CT scanner may include a PET image and a CT image, and both two images may be used in the analysis.

The distribution curve acquisition unit 120 acquires a time-radiation dose distribution curve, which represents a radiation dose for each organ of a human body over time, from the dynamic medical images (S200).

The distribution curve acquisition unit 120 divides the diagnostic medical image based on the CT image by a predefined way, sets a boundary between an organ and a region-of-interest based on anatomical information acquired through the CT image, and acquires a radiation dose of a radioactive isotope and a position of each divided region based on the PET image over time.

Figure 3:
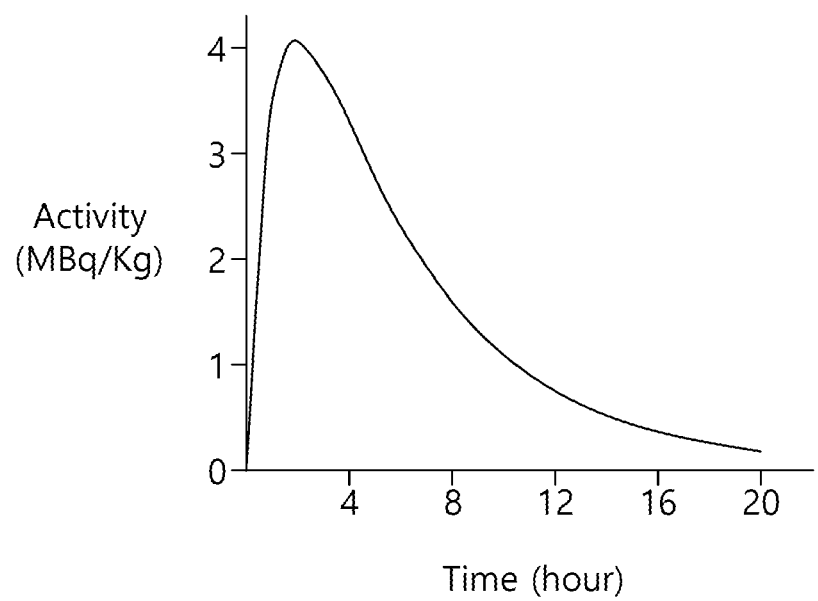
FIG. 3 is a graph of illustrating a time-radiation dose distribution curve.

FIG. 3 is a graph of illustrating a time-radiation dose distribution curve.

Referring to the graph of FIG. 3, the time-radiation dose distribution curve shows the radiation dose measured in a specific organ or a specific region over time. In the graph of the time-radiation dose distribution curve, the x-axis represents time, and the y-axis represents the measured radiation dose.

Referring back to FIGS. 1 and 2, the descriptions will be continued.

Eventually, the distribution curve acquisition unit 120 acquires a diagnostic distribution curve based on time-radiation dose distribution for each organ region of a human body from the dynamic medical images acquired after injecting the radiopharmaceuticals into the patient.

The dynamic medical image acquisition unit 110 and the distribution curve acquisition unit 120 acquire the dynamic medical images of various patients and the time-radiation dose distribution curves according to the organs, and transmit the acquired dynamic medical images and the acquired time-radiation dose distribution curves according to the organs to the deep learning network 130 (to be described later) for the deep learning.

The deep learning network 130 includes a deep learning unit 131, and an image generation unit 132.

Here, the deep learning is defined as a set of machine learning algorithms that attempt high-level abstractions through a combination of several nonlinear transformation techniques, and broadly refers to a field of machine learning that trains a computer in a human's way of thinking. The machine learning is based on an artificial neural network (ANN) to make a computer learn a lot of data by itself like a human. The deep learning trains a computer to distinguish and classify objects by imitating an information processing method of a human brain that discovers a pattern in a lot of data and distinguishes objects. By the deep learning, a computer can make recognition, inference, and decision on its own without any criteria set by a human. The deep learning may be widely used, for example, in recognizing, analyzing, classifying, etc. an image.

According to the disclosure, a generative adversarial network (GAN) algorithm may be used to generate medical images corresponding to time other than the time the static medical images are taken, after learning the dynamic medical images collected from various patients. The GAN algorithm may generate optimal medical images corresponding to time other than the time the static medical images are taken, based on competition between a model of generating a fake that looks real and a model of identifying its authenticity. During the deep learning based on the GAN algorithm, the optimal medical images may be generated in consideration of the time-radiation dose distribution curve by learning the dynamic medical images and at the same time learning the time-radiation dose distribution curves according to the organs related to the dynamic medical images.

Ultimately, the GAN algorithm makes it possible to acquire the medical images corresponding to the entire time from the static medical images as if the dynamic medical images are taken.

To this end, the deep learning unit 131 of the deep learning network 130 applies the deep learning to the dynamic medical images collected from multiple patients and the corresponding time-radiation dose distribution curve through the deep learning network (S300). In this case, as described above, the medical images may be generated by the GAN algorithm according to the dynamic medical images and the corresponding time-radiation dose distribution curve.

Meanwhile, the static medical image acquisition unit 140 acquires the static medical images for a specific period of time after injecting radiopharmaceuticals to a specific patient (S400). The acquired static medical image is transmitted to the deep learning network 130.

The image generation unit 132 of the deep learning network 130 predicts and generates the medical images corresponding to times before and after taking the static medical images (S500). The image generation unit 132 of the deep learning network 130 is capable of predicting and generating the medical images corresponding to time other than the time the static medical images are taken, thereby generating the medical images corresponding to the entire time as if the dynamic medical images are taken.

The spatial distribution image acquisition unit 150 acquires the spatial distribution image of the radiopharmaceuticals from the static medical images and the medical images generated through the deep learning network 130 (S600).

Last, the distribution curve predictor 160 acquires a radiation dose and a position of each region over time from the acquired spatial distribution image, thereby acquiring the time-radiation dose distribution curve (S700). There is a difference in that time-radiation dose distribution curve acquired in operation S200 is a distribution curve acquired from the dynamic medical images, but the time-radiation dose distribution curve acquired in operation S700 is a distribution curve acquired from the medical images generated corresponding to time other than the time the static medical images are taken.

FIG. 4 is a view illustrating that an image is generated for each time from the static medical image and a time-radiation dose distribution curve is extracted.

Referring to FIG. 4, the first row shows the dynamic medical images taken for all the times of interest, and the other three rows below show the static medical images taken only for specific times.

In the case of the dynamic medical images on the first row, a boundary between an organ and a region-of-interest is set based on anatomical information acquired through the CT image, and a radiation dose of a radioactive isotope and a position of each divided region are acquired based on the PET image over time, thereby finally acquiring the time-radiation dose distribution curve without difficulties.

On the other hand, in the case of the static medical images on the second to fourth rows, the medical images are present only for some time, and therefore the time-radiation dose distribution curve corresponding to the entire time is not acquired.

In this case, the deep learning network 130 is used to generate the medical images corresponding to all the points of time before and after the acquired images, and the generated medical images and the previously acquired static medical images are analyzed, thereby predicting the time-radiation dose distribution curve.

The disclosure may be embodied by a method, an apparatus, a system, etc. The method of the disclosure may also be implemented as a program, a code, an application, software, etc. readable by a computer in a computer readable recording medium. When implemented and executed by the software or application, the elements of the disclosure are programs or code segments that execute necessary tasks. The programs or code segments may be stored in the computer readable recording medium, or may be transmitted by a computer data signal combined with a carrier through a transmission medium or a communication network.

The computer readable recording medium may include any kind of recording device in which data readable by a computer system is stored. Examples of the computer readable recording medium may include a hard disk, a floppy disk, a magnetic medium such as a magnetic tape, an optical recording medium such as a compact disc read only memory (CD-ROM), a digital versatile disc (DVD), a magneto-optical media such as a floptical disk, a random-access memory (RAM), a read-only memory (ROM), a flash memory, or the like hardware device specially configured to store and perform a program instruction. Further, the computer readable recording medium may also be distributed over network coupled computer systems such that the computer readable code is stored and executed in a distributed manner Although the disclosure has been described above with reference to embodiments depicted in the accompanying drawings, the description is for illustrative purposes only, and thus various changes and modifications can be made by a person having ordinary skill in the art to which the disclosure pertains. Therefore, the scope of the disclosure is defined by the appended claims, and it will be understood that all technical ideas in the same and equivalent scope also fall within the scope of the disclosure.

The invention claimed is:

1. A radiopharmaceutical distribution image generation system using deep learning, the system comprising:
    a dynamic medical image acquisition unit configured to acquire dynamic medical images by continuously collecting medical images of a patient concurrently with injection of radiopharmaceuticals;
    a distribution curve acquisition unit configured to acquire a time-radiation dose distribution curve, which represents a radiation dose for each organ of a human body over time, from the dynamic medical images;
    a static medical image acquisition unit configured to acquire static medical images for a specific period of time after the injection of the radiopharmaceuticals;
    a deep-learning image generation network configured to predict and generate medical images corresponding to times before and after the static medical images by collecting and learning the dynamic medical images of multiple patients and the corresponding time-radiation dose distribution curve; and
    a spatial distribution image acquisition unit configured to acquire a spatial distribution image of the radiopharmaceuticals from the static medical images and the generated medical images,
    wherein the deep learning network comprises:
    a deep learning unit configured to collect and learn the dynamic medical images of the multiple patients and the corresponding time-radiation dose distribution curve; and
    an image generation unit configured to predict and generate the medical images corresponding to times before and after the static medical images are taken.

2. The system of claim 1, wherein the deep learning network uses a generative adversarial network (GAN) to generate the medical images according to the dynamic medical images and the corresponding time-radiation dose distribution curve.

3. The system of claim 1, further comprising a distribution curve predictor configured to acquire the time-radiation dose distribution curve by acquiring a radiation dose and a position of each region over time from the spatial distribution image.

4. A method performed by a radiopharmaceutical distribution image generation system using deep learning, the method comprising:
    acquiring dynamic medical images by continuously collecting medical images of a patient concurrently with injection of radiopharmaceuticals;
    acquiring a time-radiation dose distribution curve, which represents a radiation dose for each organ of a human body over time, from the dynamic medical images;
    collecting the dynamic medical images of multiple patients and the corresponding time-radiation dose distribution curve and learning through a deep learning network;
    acquiring static medical images for a specific period of time after the injection of the radiopharmaceuticals;
    predicting and generating medical images corresponding to times before and after the static medical images through the deep learning network; and
    acquiring a spatial distribution image of the radiopharmaceuticals from the static medical images and the generated medical images,
    wherein the deep learning network comprises:
    a deep learning unit configured to collect and learn the dynamic medical images of the multiple patients and the corresponding time-radiation dose distribution curve, and
    an image generation unit configured to predict and generate the medical images corresponding to times before and after the static medical images are taken.

5. The method of claim 4, wherein the deep learning network uses a generative adversarial network (GAN) to generate the medical images according to the dynamic medical images and the corresponding time-radiation dose distribution curve.

6. The method of claim 4, further comprising acquiring the time-radiation dose distribution curve by acquiring a radiation dose and a position of each region over time from the spatial distribution image.

* * * * *